(12) United States Patent
Miller et al.

(10) Patent No.: US 6,234,965 B1
(45) Date of Patent: *May 22, 2001

(54) METHODS AND APPARATUS FOR IMPROVING BIOCHEMICAL BASED THERAPY IN HUMANS

(75) Inventors: Steven L. Miller, Pacifica; Michael M. Merzenich, San Francisco; Bret E. Peterson, Lafayette, all of CA (US)

(73) Assignee: Scientific Learning Corporation, Berkeley, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,838

(22) Filed: Mar. 31, 1998

(51) Int. Cl.[7] ....................................... A61B 5/00
(52) U.S. Cl. .............................................. 600/300
(58) Field of Search ...................... 600/300; 364/413.02; 436/63

(56) References Cited

U.S. PATENT DOCUMENTS

| | | | |
|---|---|---|---|
| 4,839,822 | * | 6/1989 | Dornord et al. ...................... 600/300 |
| 4,996,988 | * | 3/1991 | Ohhara et al. ......................... 600/300 |
| 5,678,571 | | 10/1997 | Brown .................................. 128/898 |
| 5,722,418 | | 3/1998 | Bro ..................................... 128/732 |
| 5,725,472 | | 3/1998 | Weathers ............................... 600/21 |
| 5,776,055 | * | 7/1998 | Haye .................................... 600/300 |
| 5,910,107 | | 6/1999 | Iliff ...................................... 600/300 |
| 5,913,310 | | 6/1999 | Brown .................................. 128/897 |

FOREIGN PATENT DOCUMENTS

| | | | |
|---|---|---|---|
| WO 93/02622 | 2/1993 | (WO) | .............................. A61B/5/16 |
| WO 94/04072 | 3/1994 | (WO) | .............................. A61B/5/00 |
| WO 94/06088 | 3/1994 | (WO) | .............................. G06F/15/42 |
| WO 95/29447 | 11/1995 | (WO) | .............................. G06F/15/02 |
| WO 97/06730 | 2/1997 | (WO) | .............................. A61B/5/0484 |
| WO 97/34526 | 9/1997 | (WO) | .............................. A61B/5/05 |

OTHER PUBLICATIONS

Roger Jelliffe, et al., Adaptive control of drug dosage regimens: basic foundations, relevant issues, and clinical examples, International Journal of Bio–Medical Computing 36, (pp. 1–23), © 1994.

(List continued on next page.)

Primary Examiner—Max Hindenburg
(74) Attorney, Agent, or Firm—Beyer Weaver & Thomas, LLP (57) ABSTRACT

A computer-implemented method for improving biochemical-based therapy, or other forms of therapy such as surgery or radiation, in a human. Using the biochemical-based therapy for discussion, the computer-implemented method may include administering, using a computer, a first stimulus/response exercise to the human to measure at least one of an efficacy of the biochemical portion on the human and an undesirable side effect of the biochemical portion on the human. If the administering the first stimulus/response exercise measures the efficacy of the biochemical portion on the human, the method further includes improving the efficacy of the biochemical portion on the human by identifying a second stimulus/response exercise that at least maintains the efficacy of the biochemical portion on the human, and administering, using the computer, the second stimulus/response exercise to the human. If the administering the first stimulus/response exercise measures the undesirable effect of the biochemical portion on the human, reducing the undesirable effect of the biochemical portion on the human by identifying a third stimulus/response exercise that reduces the undesirable side effect of the biochemical portion on the human, and administering, using the computer, the third stimulus/response exercise to the human.

24 Claims, 3 Drawing Sheets

OTHER PUBLICATIONS

Schneider et al. Self–Regulation of Slow Cortical Potentials in Psychiatric Patients: Schizophrenia, © Dec. 1992, Biofeedback and Self–Regulation, vol. 17, No. 4, pp. 277–292.

Tretter F., Perspectives of Computer–Aided Therapy and Rehabilitation in Psychiatry, Jul. 1996, pp. 475–486.

Hermanutz M. and Gestrich J., Computer–assisted Attention Training in Schizophrenics, 1991, European Archives of Psychiatry and Clinical Neuroscience, vol. 240, pp. 282–287.

Nagarajan et al., "Practice–Related Improvements in Somatosensory Interval Discrimination Are Temporally Specific But Generalize Across Skin Location, Hemisphere, and Modality," Feb. 15, 1998, The Journal of Neuroscience, pp. 1559–1570.

Miller et al., "Improvements in Language Abilities with Training of Children With Both Attentional and Language Impairments," Oct. 1997, Society for Neuroscience Reprint Series vol. 23, p. 490.

Merzenich et al., "Temporal Processing Deficits of Language–Learning Impaired Children Ameliorated by Training," Jan. 5, 1996, Science vol. 271, pp. 77–81.

* cited by examiner

METHODS AND APPARATUS FOR IMPROVING BIOCHEMICAL BASED THERAPY IN HUMANS

BACKGROUND OF THE INVENTION

The present invention relates to techniques for improving biochemical-based therapy in a human. More particularly, the present invention relates to computer-implemented techniques for employing task-controlled behavioral assessment and behavioral training, such as stimulus/response exercises or games, to improve the efficacy of the biochemical-based therapy to reduce or eliminate the need thereof, or to reduce the undesirable side effects of the biochemical-based therapy in a human.

The use of biochemical-based therapy involving various biological and/or chemical compounds to address a physiological and/or mental condition in humans is known. Generally speaking, biochemical-based therapy involves repeatedly administering a preset dosage of a biological/chemical compound to a human (by injection, ingestion, transdermal techniques, and/or the like) over a period of time to improve the aforementioned physiological and/or mental condition. By stimulating the human in a pharmacological manner, it is often hoped that over time the physiological and/or mental condition to be addressed would improve to the point where the biochemical-based therapy is no longer needed.

Figure 1:
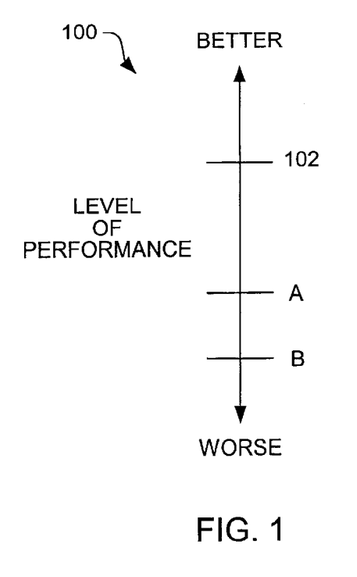
FIG. 1 depicts, to facilitate discussion, a performance scale of a particular condition in human, including the acceptable level of performance and the levels of performance of humans A and B.

To facilitate discussion, scale 100 of FIG. 1 represents a scale of performance level relating to a particular physiological and/or mental condition (such as, for example, attention span) on which a desired condition 102 represents the level of performance acceptable and/or desirable in a human. On scale 100, the levels of performance by a human A and a human B are shown. As depicted, the levels of performance of humans A and B fall short of desired condition 102. To bring the levels of performance of humans A and B closer to desired condition 102, the prior art biochemical-based therapy may involve administering preset dosages of a biological and/or chemical compound over a predefined period of time to human A and human B. By driving the improvement in a pharmacological manner, it is commonly hoped that over time the level of performance of humans A and B in this particular condition (e.g., attention span) may improve to the point where the dosages of biological and/or chemical compound may be reduced or terminated altogether.

It has been found, however, that when the improvement in human is driven solely by pharmacological effects of the administered biological/chemical compounds, humans tend to develop a tolerance condition, which over time may actually require an increase in the required dosage of the biological/chemical compounds administered.

Figure 2A:
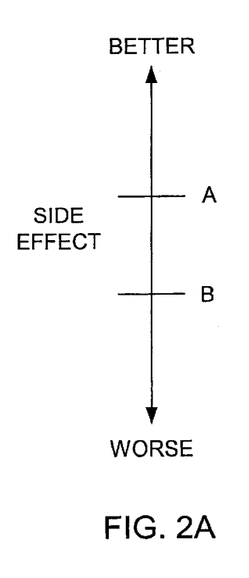
FIG. 2A depicts the performance of scale of a condition impacted by the prior art biochemical-based therapy as an unwanted side effect, including the acceptable level of performance and the levels of performance by humans A and B.

Furthermore, for many administered biological/chemical compounds, there are side effects which must be tolerated and/or addressed with even more biochemical-based therapy (e.g., by administering yet other biological/chemical compounds to address the side effects). With reference to FIG. 2A, scale 200 represents the scale of performance pertaining to a particular condition of the human, which condition may be impacted as an undesirable side effect of the biochemical-based therapy administered to address the first ailment or deficit (e.g., such as the attention deficit condition of the example of FIG. 1). Scale 200 may represent, for example, the level of sleepiness or hand shaking in the human subject.

Figure 2B:
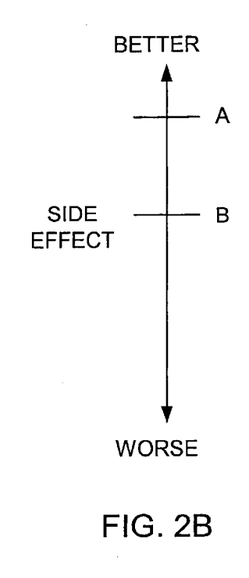
FIG. 2B depicts the levels of performance of humans A and B on the scale of FIG. 2A after the unwanted side effect is treated with biological/chemical compounds.

In FIG. 2A, the intrinsic levels of sleepiness, i.e., the levels of sleepiness in the absence of the biochemical-based therapy, of humans A and B are shown. In FIG. 2B, the administration of the biochemical-based therapy to address the related attention deficit condition has undesirably increased the levels of sleepiness in humans A and B. As mentioned earlier this undesirable side effect just, in the prior art, either be tolerated (such as avoiding driving) or addressed with yet more biochemical-based therapy (such as ingesting caffeine).

Furthermore, it is recognized that even if immediate side effects are not observed in connection with a given biochemical-based therapy regime, there are lingering concerns regarding the long term effects associated with the administration of biological/chemical compounds which may not be naturally produced by human. Accordingly, recent trends have shown an increased reluctance on the part of people to continue a biochemical-based therapy program for an extended period of time and/or to take increasing dosages of biological/chemical compounds (due to, e.g., the aforementioned tolerance problem) to address a particular physiological and/or mental condition.

In view of the foregoing, there are desired improved techniques for improving the efficacy of the biological/chemical compounds employed in biochemical-based therapy and/or for reducing the undesirable side effects thereof without employing additional biochemical-based therapy.

SUMMARY OF THE INVENTION

The invention relates, in one embodiment, to a computer-implemented method for improving biochemical-based therapy, or other forms of therapy such as surgery or radiation, in a human. By way of example, biomedical-based therapy may include repeatedly administering a biochemical portion (e.g., a biological and/or a chemical compound) to the human. Using the biochemical-based therapy for discussion, the computer-implemented method may include administering, using a computer, a first stimulus/response exercise to the human to measure at least one of an efficacy of the biochemical portion on the human and an undesirable side effect of the biochemical portion on the human. If the administering the first stimulus/response exercise measures the efficacy of the biochemical portion on the human, the method further includes improving the efficacy of the biochemical portion on the human by identifying a second stimulus/response exercise that at least maintains the efficacy of the biochemical portion on the human, and administering, using the computer, the second stimulus/response exercise to the human.

If the administering the first stimulus/response exercise measures the undesirable effect of the biochemical portion on the human, reducing the undesirable effect of the biochemical portion on the human by identifying a third stimulus/response exercise that reduces the undesirable side effect of the biochemical portion on the human, and administering, using the computer, the third stimulus/response exercise to the human. It should be appreciated that the above discussion applies to other types of therapy (e.g., radiation) and that the stimulus/responses are not limited to behavioral responses (e.g., the stimulus and responses may also include responses that are physiological in nature).

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which like reference numbers refer to like items and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In accordance with one aspect of the present invention, there is provided a computer-implemented technique for improving the efficacy of and/or for reducing the undesirable side effects of the biological/chemical compounds employed in a biochemical-based therapy program. In the preferred embodiment, the computer-implemented technique of the present invention involves employing stimulus/response exercises or games that are specifically selected to improve the intrinsic level of performance of a human in a particular condition of interest (e.g., attention span) so that the dosages of biological/chemical compounds required in the biochemical-based therapy regime become progressively smaller or eliminated all together over time. To put it differently, the computer-implemented technique of the present invention simulates the pharmacological effects of the administered biological/chemical compounds to drive the improvement in the level of performance without actually employing a biological/chemical compound.

While not wishing to be bound by theory, it is believed that when a human is trained in a particular behavioral training regime, the connections among relevant cells are strengthened such that the intrinsic level of performance (i.e., the level of performance that exists in the absence of the biological/chemical usage) related to the targeted condition increases. Over time, behavioral training may increase the intrinsic level of performance of the targeted condition to the point where it is possible to reduce or eliminate the need for the biological/chemical compound of the biochemical-based therapy.

In accordance with one hypothesis, cells may be thought of as being packed together closely in human. The cells compete for resources such as minerals or chemicals, which are needed for cell maintenance and growth. Synchronized activities between groups of cells invigorate connection strengths and stimulate access to resources by those cells. On the other hand, groups of cells that do not participate in synchronized activities are less competitive, have weaker inputs because they have less vigorous connections and thereby have less access to the resources. It is believed that behavioral training using stimulus/response exercises improves the coincident input-dependent activities (and synchronization) between groups of cells, thereby improving their functionality and vigor and their access for the highly competitive resources needed for cell growth and/or maintenance. In other words, the administration of stimulus/response exercises modifies the cells in a physical way, i.e., they form and strengthen connections between them in a way that cells that are not similarly simulated do not.

With a biochemical-based therapy regime based solely on the administration of preset dosages of biological/chemical compounds (as was done in the p/a), it is believed that the biological/chemical compounds simulate the synchronized connections between groups of cells, i.e., the human body temporarily responds as if the cells interact in a synchronized manner. But the cells themselves did not interact. Instead, they merely react, or cause the human body to react, to the pharmacological effects of the administered biological/chemical compounds. Because the cells are not actually stimulated in natural ways, the administration of the biological chemical compounds can be regressive, causing the human body to require ever higher dosages of the biological/chemical compounds to make up for the deficiencies in activity and vigor. Over time, tolerance to the administered biological/chemical compounds occurs, sometimes to the point where the administered biological/chemical compounds are no longer effective irrespective of the dosage.

It is appreciated by the inventors herein that, contrary to conventional theories, the human brain is not hard-wired even in adult humans, and that the connections between cells are quite plastic and can be manipulated, modified, and/or strengthened through targeted behavioral training. It is further appreciated by the inventors herein that there is a cause-and-effect relationship, albeit a non obvious one, between stimulus/response exercises and the efficacy of the administered biological/chemical compounds. From these insights, it is further appreciated that a behavioral training regime employing for example stimulus/response exercises, may be administered to a human to specifically target and strengthen the synchronized activities between groups of cells to stimulate the improvement of a physiological and/or mental condition in the human so as to reduce and/or eliminate over time the required dosages of biological/chemical compounds of the prior art biochemical-based therapy. Since a behavioral training programs can be targeted with much greater precision than a biochemical-based therapy program, the use of behavioral training to improve the biochemical-based therapy advantageously reduces the possibility of undesirable and/or unpredictable side effects before, during, and/or after the implementation of the training program.

Figure 3:
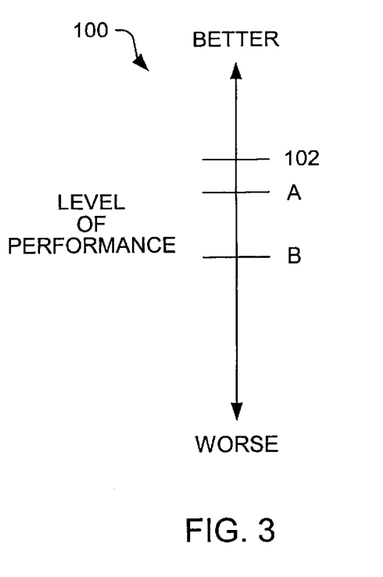
FIG. 3 depicts the intrinsic levels of performance of humans A and B on the scale of FIG. 1 after a behavioral training program is employed.

The features and advantages of these aspects of the invention, as well as other aspects of the present invention, may be better understood with reference to the figures and discussions that follow. FIG. 3A depicts scale 100 of FIG. 1, along with desired condition 102. In the illustration of FIG. 3, the intrinsic levels of performance of humans A and B are shown to have moved closer toward desired condition 102 via targeted stimulus/response exercises, which have been administered over time to humans A and B. Because of the improvement driven by the targeted behavioral modification training, the dosages of biological/chemical compounds required by the human may be reduced or eliminated altogether. By way of example, the intrinsic level of performance of human A in the targeted condition (e.g., attention span) may have improved via behavioral training to the point where it is no longer necessary to administer the biological/chemical compound of the biochemical-based therapy program to human A. The intrinsic level of performance of human B may also have increased through behavioral training such that the required dosage is substantially reduced. In effect, behavior training may be employed to improve the efficacy of the administered biological/chemical compounds on the human. Because a behavioral training program can be targeted at the condition to be remedied and typically does not affect other conditions/areas in the way that biological/chemical compounds do in humans, such improvement advantageously does not come at the expense of undesirable and/or unwanted side effects.

As mentioned, behavioral training via stimulus/response exercises may also be employed to reduce undesirable side effects of the biochemical-based therapy and/or of other types of therapy such as surgery, radiation, or the like. To simplify the discussion herein, only the side effects of biochemical-based therapy will be discussed in greater detail. It should be understood, however, that the techniques disclosed herein also apply to reduce undesirable side effects from other types of therapy as well (e.g., other environmental or procedures such as surgery or radiation).

Figure 4:
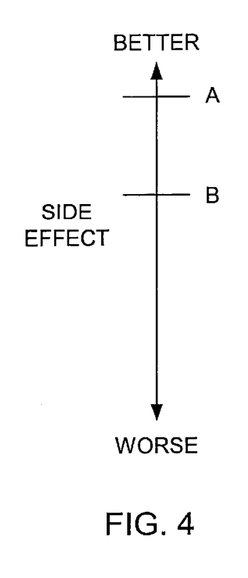
FIG. 4 depicts the intrinsic levels of performance of humans A and B on the scale of FIG. 2A after a behavioral training program is employed, showing that the side effect is reduced.

FIG. 4 illustrates scale 200 of FIGS. 2A and 2B, which represents a condition undesirably affected by the administration of the biological/chemical compound to address the primary condition of FIG. 1. In FIG. 4, targeted behavioral modification training (via stimulus/response exercises) have decreased the undesirable side effects such that the intrinsic level of side effects (i.e., the level of side effect that exists in the absence of any biochemical-based therapy to address the side effects) is reduced. As in the case of FIG. 3, the reduction of the undesirable side effects may be sufficient to either reduce any need to address them via another biochemical-based therapy program or to eliminate such need altogether.

The reduction in the intrinsic level of undesirable side effect is possible since the behavioral modification training can be specifically targeted such that improvement in one condition may be achieved without adversely impacting other conditions in the human. This is unlike the prior art approach wherein the consumption of biological/chemical compounds may affect different groups of cells in sometimes undesirable and unpredictable manners. As such, it is possible to reduce the undesirable side effects without causing yet other side effects and/or reducing the effectiveness of the biochemical-based therapy program (or the behavioral training program) administered to the address the original condition (e.g., the attention deficit condition).

Figure 5:
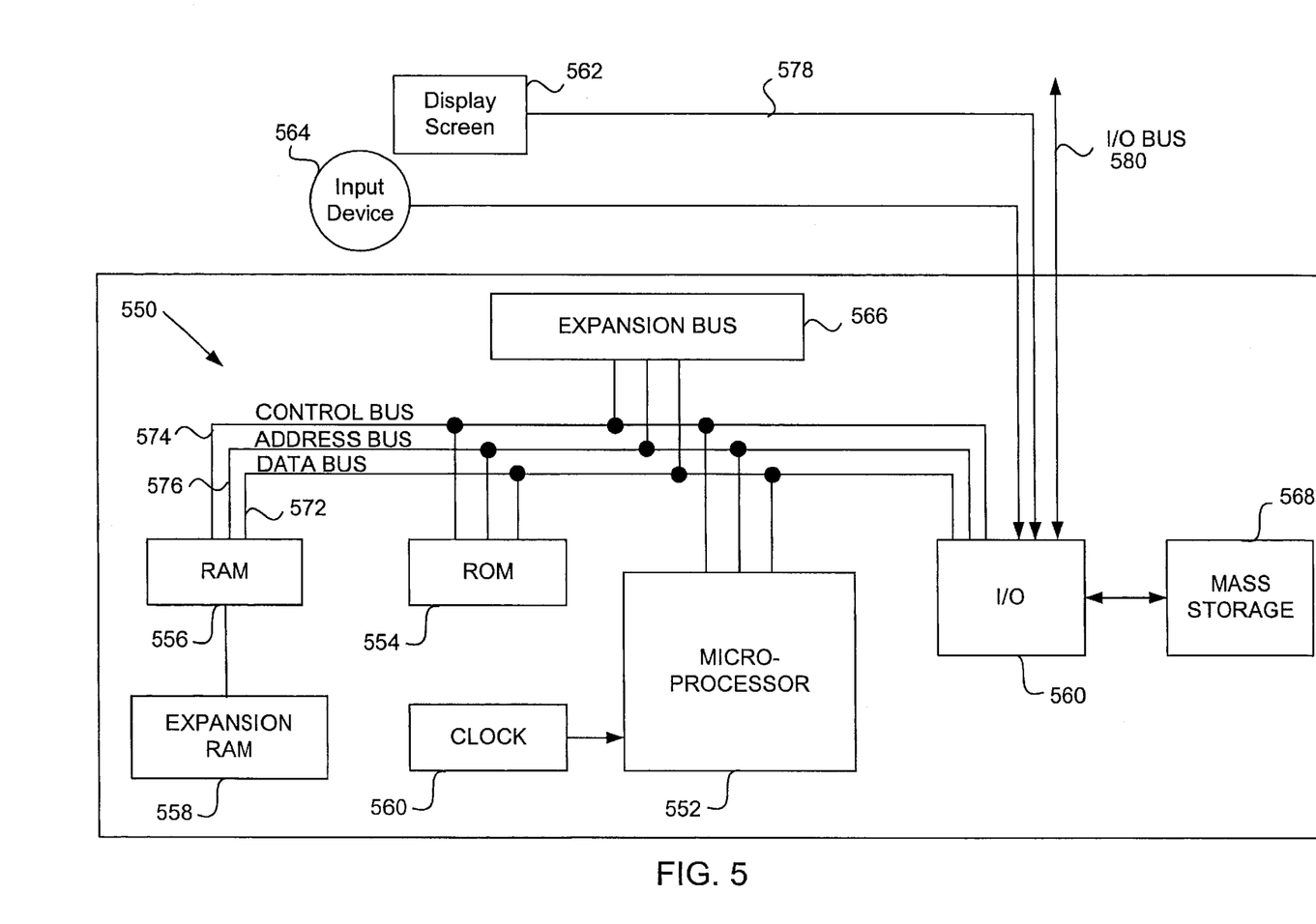
FIG. 5 illustrate, in accordance with one embodiment of the invention, the computer-controlled apparatus for administering behavioral training to human to improve the biochemical-based therapy.

As mentioned, the behavioral training program is preferably administered using a computer-implemented technique. FIG. 5 illustrates, in accordance with one embodiment of the invention, an exemplary computer-controlled apparatus, including computer 550, for delivering computer-controlled stimuli to the human subject to improve the biochemical-based therapy. Depending on the behavioral training regime chosen, the stimulus may be delivered through any of the senses or a combination thereof. Responses from the human subject may be received by the computer and evaluated in any number of ways, some of which are discussed further below.

Referring to FIG. 5, a computer system 550 in accordance with one embodiment of the present invention includes a central processing unit (CPU) 552, read only memory (ROM) 554, random access memory (RAM) 556, expansion RAM 558, input/output (I/O) circuitry 560, display assembly 562, input device 564, and expansion bus 566. Computer system 550 may also optionally include a mass storage unit 568 such as a disk drive unit or nonvolatile memory such as flash memory and a real-time clock 560. In one embodiment, mass storage unit 568 may include units which utilizes removable computer readable media, such as floppy disks, opto-magnetic media, optical media, and the like for the storage of programs and data.

CPU 552 is preferably a commercially available, single chip microprocessor such as one of the Intel X86 (including Pentium™) or Motorola 680XX family of chips, a reduced instruction set computer (RISC) chip such as the PowerPC™ microprocessor available from Motorola, Inc, or any other suitable processor. CPU 552 is coupled to ROM 554 by a data bus 572, control bus 574, and address bus 576. ROM 554 may partially contain the basic operating system for the computer system 550. CPU 552 is also connected to RAM 556 by busses 572, 574, and 576 to permit the use of RAM 556 as scratch pad memory. Expansion RAM 558 is optionally coupled to RAM 556 for use by CPU 552. CPU 552 is also coupled to the I/O circuitry 560 by data bus 572, control bus 574, and address bus 576 to permit data transfers with peripheral devices.

I/O circuitry 560 typically includes a number of latches, registers and direct memory access (DMA) controllers. The purpose of I/O circuitry 560 is to provide an interface between CPU 552 and such peripheral devices as display assembly 562, input device 564, mass storage 568, and/or any other I/O devices. I/O circuitry 560 may also include analog-to-digital (A/D) converters, digital-to-analog (D/A) converters, as well as other control circuits for controlling and receiving feedback data from the I/O devices. The I/O devices suitable for generating stimuli to be administered to the human subject and for receiving responses therefrom may be coupled to I/O bus 580 of computer 550. Display assembly 562 of computer system 550 is an output device for displaying objects and other visual representations of data, as well as for generating visual stimuli in one embodiment.

The screen for display assembly 562 can be a device that uses a cathoderay tube (CRT), liquid crystal display (LCD), or the like, of the types commercially available from a variety of manufacturers. Input device 564 can be a keyboard, a mouse, a stylus working in cooperation with a position-sensing display, or the like. Alternatively, input device 564 can be an embedded RF digitizer activated by an "active" RF stylus. As a further alternative, input device 564 may be any type of switch capable of communicating a test subject's response to computer system 550. Therefore, as used herein, the term input device will refer to any mechanism or device for entering data and or pointing to a particular location on a screen of a computer display. One or more input devices may be provided to control computer 550 and/or to receive responses from the test subject. Note that the responses to be received and employed in the behavioral training program may include not only behavioral responses (e.g., behaviors exhibited by the human subject such as clicking on a mouse) but also physiological responses (e.g., EKG, EEG, MEG, or any other measurable physiological responses). The aforementioned input devices, appropriately chosen for the response to be obtained, are available from a variety of vendors and are well known in the art.

Some type of mass storage 568 is generally considered desirable. However, mass storage 568 can be eliminated by providing a sufficient amount of RAM 556 and expansion RAM 558 to store user application programs and data. It is generally desirable to have some type of long term mass storage 568 such as a commercially available hard disk drive, nonvolatile memory such as flash memory, battery backed RAM, PC-data cards, or the like.

The stimuli generators may include headphones (for delivering auditory stimuli), computer-controlled probes (for delivering touch stimuli), visual stimuli generators (for delivering visual stimuli), physiological stimulatory generation or probes (which may be internally or externally placed) and/or virtual reality apparatus (for delivering stimuli to and receiving responses from the human subject in a virtual manner through any of the senses). In general, these stimuli generators may interface with computer system 550 via an appropriate interface circuit, which may be either internal or external to computer 550 and/or dedicated to the I/O device. A visual stimuli generator may be implemented by, for example, any light generating device such as a light bulb, a flash device, another computer display screen or the like if such is employed instead of display screen 562 of computer 550 for providing visual stimuli to the test subject. The virtual reality apparatus may be implemented by, for example data gloves, virtual goggles, data-enabled body suits, or the like, each of which may be able to both deliver the stimuli to the test subject as well as sense the responses therefrom. An optional input device, such as a switch, may also be provided for receiving responses from the test subject. The optional input device may be provided when it is desired to receive responses to the test stimuli from the test subject through an input device other than input device 564 of computer 550.

In operation, computer system 550 is employed to generate control signals to the stimuli generator(s) to produce the stimuli of the various training or condition assessment regimes. Different behavioral-based assessment/training regimes may employ stimuli having different intensity, duration, and spatial parameters, and these parameters may be varied as desired even in the same training regime or even during a given training session. These stimuli are then finished to the test subject for assessment and/or training, and the responses from the test subject may then be recorded by an input device and analyzed by CPU 552 (for accuracy, delay, or other parameters indicative of the subject's level of performance). If desired, feedback to the test subject may be given at various stages of the test(s) via, for example, display assembly 562.

It should be borne in mind that although computer system 550 is discussed in some detail herein to facilitate discussion, the invention may be practiced using a variety of suitable computer-implemented technique. In general, any suitable computer system may be employed for generating control signals to the stimuli generators and receive feedback from the input device(s). Further, the inventive training technique disclosed herein may be implemented via a computer network, such as a local area network (LAN), wide area network (WAN) or a global computer network such as the Internet. In the latter cases, the inventive computer implemented behavioral training technique may be implemented at least in part as downloadable computer software and data (e.g., applets such as JAVA™ applets from Sun Microsystems Inc. or ActiveX from Microsoft Corp. of Redmond, Wash.). The downloadable computer software and data may be kept on one or more servers on the network, accessible by any client computer or terminal capable and authorized for such access. The client computer/terminal may then be employed to control an appropriate stimuli generator and to gather responses from the test subject. To facilitate assessment and/or training, the downloadable computer software and data can be downloaded once and reused over and over at the client computer/terminal. Alternatively, the downloadable computer software and data can be downloaded for each individual session via the network as needed. In some cases, the computer software may be executed at the servers themselves, with program outputs transmitted to the client computer/terminal for interfacing with the I/O devices. Network computing techniques and implementations therefor are well known in the art and are not discussed in great detail here for brevity's sake.

Figure 6:
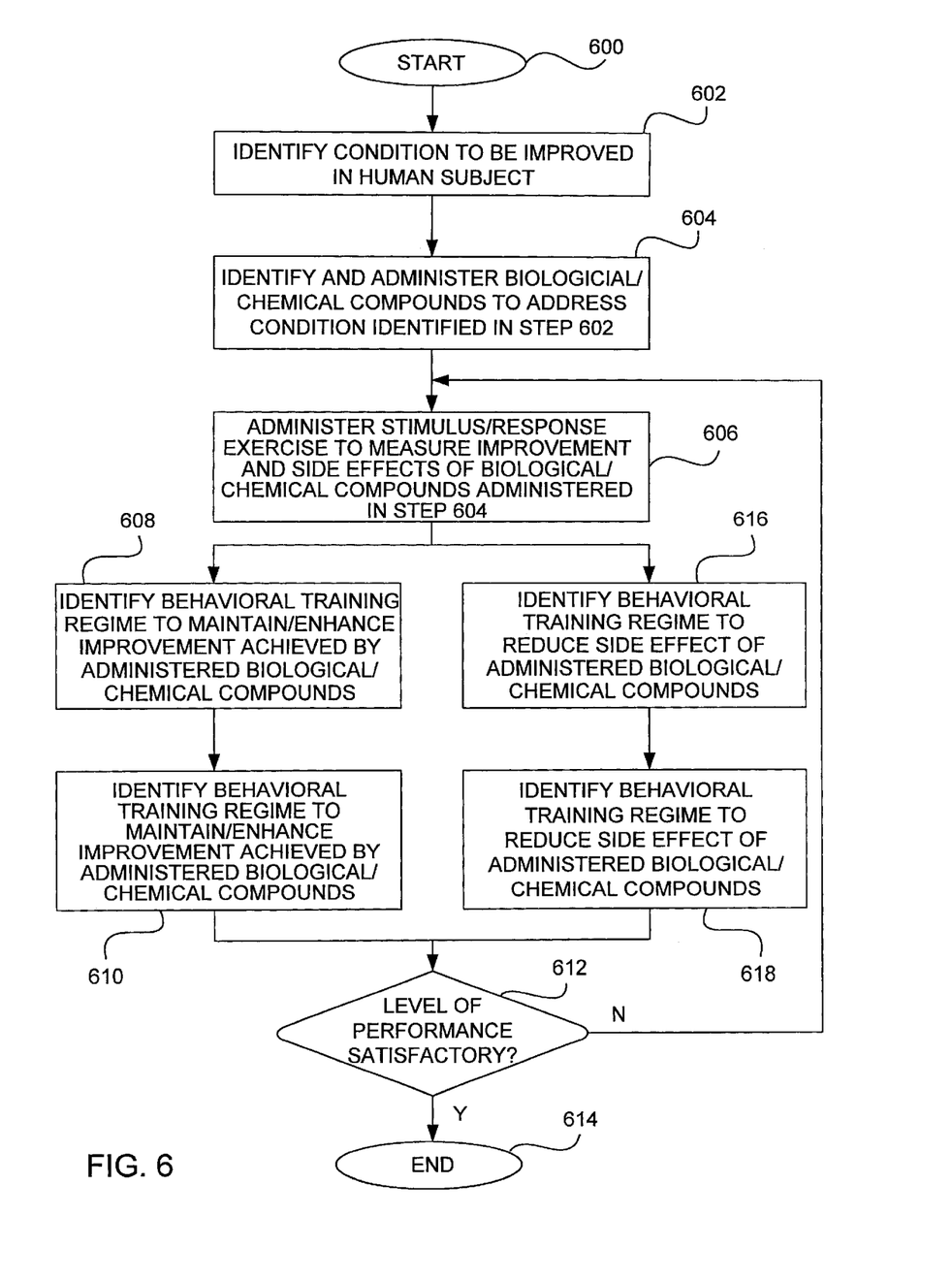
FIG. 6 illustrates, in accordance with one embodiment of the invention, the steps of the computer-implemented behavioral training that is capable of improving the efficacy of the biochemical-based therapy and/or reducing the side effects thereof.

FIG. 6 illustrates, in accordance with one embodiment of the present invention, the major steps of the computer-implemented method for improving the biochemical-based therapy in a human. Note that since these steps may be performed over time, each step may be accomplished, in the same or different iterations of the computer-implemented technique, in the same computer/terminal or in a similarly enabled computer/terminal. Accordingly the term "computer" as employed herein should be construed to cover any computer or terminal that is capable of performing the disclosed step under discussion and does not necessarily limit the application of the entire sequence of steps to any single computer or terminal (i.e., the different steps may be performed on different computers or on a single computer as convenient and/or appropriate.

In step 602, a stimulus/response exercise or a battery of stimulus/response exercises is administered to the human to identify the condition or conditions to improve. Step 602 is optional since there exists other diagnostic techniques in the art to identify a particular ailment or deficiency in a human without employing the stimulus/response exercises. Such diagnostic techniques may include, for example, blood testing, radiology-based techniques, identification through symptoms exhibited by the human subject, or the like.

In step 604, a biological/chemical compound useful in addressing the condition identified in step 602 is administered in doses to the human as part of a biochemical-based therapy program. The selection of a particular biological/chemical compound useful for addressing a particular condition is conventional in the art and may be performed by consulting widely available reference works, including literature from the pharmaceutical companies.

In step 606, a stimulus/response exercise or a battery of stimulus/response exercises is administered, preferably using a computer-implemented technique, to the human to measure the improvement and side effects, if any, of the administered biological/chemical compounds. If an improvement is detected in step 606, the method proceeds to step 608 wherein the particular stimulus/response exercise (s) useful in enhancing/maintaining the improvement achieved by the administered biological/chemical compound is identified. It should be appreciated that the specific stimulus/response exercise(s) identified in step 606 varies depending on the condition to be remedied and may be derived theoretically or empirically in a laboratory setting. If attention deficit is to be remedied, for example, the exercise may involve stimulus/response games designed to hold the human's attention for ever increasing periods of time.

In step 610, the identified stimulus/response exercises of step 608 are then administered to the human, preferably as battery of exercises over time to maintain and/or enhance the improvement achieved by the biological/chemical compound administered in step 606.

In step 612, the level of performance pertaining to the condition identified in step 602 may be measured again using a conventional testing and/or assessment technique or using an appropriate stimulus/response exercise as an assessment tool. If the level of performance is satisfactory (e.g., if the result of a stimulus/response game indicates that the human has satisfactorily improved in his ability to focus and/or pay attention over time), the method proceeds to step 614 wherein it is understood that the improvement is such that additional dosages of the biological/chemical compounds are no longer necessary.

On the other hand, if the level of performance measured in step 612 is still unsatisfactory, i.e., the intrinsic level of performance is not satisfactory in view of the desired level of performance in the particular condition in question, the method returns to step 606 wherein additional stimulus/response exercises may be administered, either alone or in conjunction with a dosage of the biological/chemical compound that is sufficient to bring the level of performance up to a predefined level of performance in this iteration.

Note that in subsequent iterations, it may be unnecessary to identify again the stimulus/response exercise(s) that is useful in maintaining and/or enhancing the improved performance since the stimulus/response exercise identified in a previous iteration on this human may be employed without requiring identifying step 608 to be undertaken for every iteration. On the other hand, it may be desirable to identify a different stimulus/response exercise in a subsequent iteration to maximize the chance of improving the biochemical-based therapy program. Thus, the same stimulus/response exercise may be employed in different iterations or different stimulus/response exercises may be employed instead.

The stimulus/response exercise may be administered again in step 610 to further improve the intrinsic level of performance. Thereafter, the method continues until the intrinsic level of performance rises to the level where the biological/chemical compound is no longer needed or where it is felt that another or different biological/chemical compound may be required.

If the administered biological/chemical compound produces an undesirable side effect (as detected in step 606), the method may proceed from 606 to step 616 wherein a stimulus/response exercise useful for reducing the undesirable side effects of the administered biological/chemical compound is identified. As in step 616, the specific stimulus/response exercise useful in reducing a particular identified side effect may vary depending on the side effect to be remedied and may be ascertained theoretically or empirically in a laboratory setting.

In step 618, the stimulus/response exercise(s) identified in step 616 that is useful for reducing the undesirable side effect of the biochemical-based therapy administered to address the original condition (e.g., attention deficit) is administered to the human. Thereafter, the level of performance of the human pertaining to this particular side effect condition (e.g., the aforementioned sleepiness, or hand shaking) is ascertained in step 606 to determine whether further training is necessary.

As can be appreciated from the foregoing, the invention advantageously improves the efficacy of the administered biological/chemical compound of the prior art biochemical-based therapy in a manner that is specifically targeted to the condition to be improved and that does not require the consumption of other biological/chemical compounds. Since the behavioral training is specifically targeted, the possibility of unwanted side effects from the behavioral training is substantially reduced. Over time, behavioral training advantageously improves the intrinsic level of performance of the human subject such that, as mentioned, the biological/chemical consumption is reduced or eliminated altogether.

The use of behavioral training to reduce the unwanted side effects of the administered biological/chemical compounds also offers similar advantages. The targeted nature of behavioral training minimizes the possibility of introducing yet other unwanted side effects when trying to reduce the first unwanted side effect. Since the reduction in unwanted side effects is accomplished without employing still more biological/chemical compounds, the invention advantageously offers another way for humans who do not wish to treat the unwanted side effect with additional biological/chemical compounds to minimize the suffering associated with unwanted side effects.

While this invention has been described in terms of several preferred embodiments, there are alterations, permutations, and equivalents which fall within the scope of this invention. By way of example, although the behavioral training is described as being performed after at least one administration of the biochemical-based therapy regime, it is also possible to employ behavioral training to reduce/eliminate the dosage prior to the administration of the biochemical-based therapy. Furthermore, although the behavioral training is described herein with reference to improving the negative consequences of administered biological/chemical compounds, the invention also applies to reducing and/or eliminating the negative consequences associated with any other biochemical or environmental therapies or procedures (such as surgery, radiation, or the like). It is therefore intended that the following appended claims be interpreted as including all such alterations, permutations, and equivalents as fall within the true spirit and scope of the present invention.

What is claimed is:

1. A computer-implemented method for improving a biochemical-based therapy in a human, said biochemical-based therapy involving repeatedly administering a biochemical portion to said human, comprising:

administering, using a computer, a first stimulus/response exercise to said human to measure an efficacy of said biochemical portion on said human;

if said administering said first stimulus/response exercise measures said efficacy of said biochemical portion on said human, improving said efficacy of said biochemical portion on said human by identifying a second stimulus/response exercise that at least maintains said efficacy of said biochemical portion on said human, and administering, using said computer, said second stimulus/response exercise to said human.

2. The computer-implemented method of claim 1 wherein said second stimulus/response exercise represents an exercise that enhances said efficacy of said biochemical portion on said human.

3. The computer-implemented method of claim 1 wherein said first stimulus/response exercise is substantially similar to said second stimulus/response exercise.

4. A computer-implemented method for improving efficacy of a therapy on a human subject, said method comprising:
   administering, using a computer, a first stimulus/response exercise to said human to measure at least one of an efficacy of said therapy on said human subject and an undesirable side effect of said therapy on said human subject;
   if said administering said first stimulus/response exercise measures said efficacy of said therapy on said human subject, improving said efficacy of said therapy on said human subject by:
      identifying a second stimulus/response exercise that at least maintains said efficacy of said therapy on said human subject, and
      administering, using said computer, said second stimulus/response exercise to said human subject; and
   if said administering said first stimulus/response exercise measures said undesirable effect of said therapy on said human subject, reducing said undesirable effect of said therapy on said human subject by
      identifying a third stimulus/response exercise that reduces said undesirable side effect of said therapy on said human subject, and
      administering, using said computer, said third stimulus/response exercise to said human subject.

5. The computer-implemented method of claim 4, wherein said therapy is a biochemical-based therapy.

6. The computer-implemented method of claim 5, wherein administering said second stimulus/response exercise is included in a training regime.

7. The computer-implemented method of claim 6, wherein said training regime is directed to reduce the dosages of said biochemical-based therapy.

8. The computer-implemented method of claim 4, wherein said therapy is a radiation therapy.

9. The computer-implemented method of claim 4, wherein administering said training regime includes visual presentation using a first computer.

10. The computer-implemented method of claim 9, wherein said administering said training regime includes visual presentation using a second computer.

11. A computer-implemented method for improving a condition for a human subject, said method comprising:
   (a) administering, using said computer-implemented approach, a first set of exercises to said human subject, said first set of exercises being configured to assess said condition for said human subject;
   (b) identifying, using said computer-implemented approach, a second set of exercises configured to improve said condition for said human subject;
   (c) administering, using said computer-implemented approach, a training regime including said second set of exercises to said human subject, said training regime being configured to improve said condition for said human subject; and
   (d) periodically repeating (a)–(c).

12. The computer-implemented method of claim 11, further including administering, using said computer-implemented approach, a third set of exercises to said human subject, said third set of exercises being configured to identify said condition for said human subject.

13. The computer-implemented method of claim 11 further including administering a diagnostic technique to identify said condition.

14. The computer-implemented method of claim 13 wherein said diagnostic technique is blood testing.

15. The computer-implemented method of claim 11 wherein said therapy is a biochemical-based therapy.

16. The computer-implemented method of claim 11 wherein said condition is a physiological condition.

17. The computer-implemented method of claim 11 wherein said condition is a mental condition.

18. The computer-implemented method of claim 17 wherein said condition is said human subject's attention span.

19. A computer-implemented method for reducing a side effect of a therapy for a human subject, said method comprising:
   (a) administering, using said computer-implemented approach, a first set of exercises to said human subject, said first set of exercises being configured to measure the level of said side effect of said therapy for said human subject;
   (b) identifying, using said computer-implemented approach, a second set of exercises configured to reduce the level of said side effect of said therapy for said human subject;
   (c) administering, using said computer-implemented approach, a training regime including said second set of exercises to said human subject, said training regime being configured to reduce the level of said side effect of said therapy for said human subject; and
   (d) periodically repeating (a)–(c).

20. The computer-implemented method of claim 19, wherein said therapy is a first biochemical-based therapy.

21. The computer-implemented method of claim 19 wherein the training regime proceeds until said therapy is no longer required.

22. The computer-implemented method of claim 19 wherein a third set of exercises is further configured to reduce the intrinsic level of said side effect of said therapy.

23. The computer-implemented method of claim 20 wherein said second set of exercises is further directed to eliminate the use of a second biochemical-based therapy for said side effect of said therapy for said human subject.

24. A computer readable medium including instructions for improving the efficacy of a therapy in a human subject, said method comprising:
   instructions for administering, using a computer, a first stimulus/response exercise to said human to measure at least one of an efficacy of said therapy on said human subject and an undesirable side effect of said therapy on said human subject;
   instructions for, if said administering said first stimulus/response exercise measures said efficacy of said therapy on said human subject, improving said efficacy of said therapy on said human subject by:

identifying a second stimulus/response exercise that at least maintains said efficacy of said therapy on said human subject, and administering, using said computer, said second stimulus/response exercise to said human subject; and instructions for, if said administering said first stimulus/response exercise measures said undesirable effect of said therapy on said human subject, reducing said undesirable effect of said therapy on said human subject by identifying a third stimulus/response exercise that reduces said undesirable side effect of said therapy on said human subject, and administering, using said computer, said third stimulus/response exercise to said human subject.

* * * * *